(12) United States Patent
Imai

(10) Patent No.: US 7,392,078 B2
(45) Date of Patent: Jun. 24, 2008

(54) RADIATION IMAGING APPARATUS

(75) Inventor: Shinji Imai, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 248 days.

(21) Appl. No.: 11/096,264

(22) Filed: Apr. 1, 2005

(65) Prior Publication Data

US 2005/0238138 A1 Oct. 27, 2005

(30) Foreign Application Priority Data

Apr. 1, 2004 (JP) ............................. 2004-108947

(51) Int. Cl.
 *A61B 6/00* (2006.01)
 *A61B 5/05* (2006.01)
(52) U.S. Cl. ........................................ 600/436; 600/428
(58) Field of Classification Search ................. 600/428; 378/95; 382/130, 132
 See application file for complete search history.

(56) References Cited

U.S. PATENT DOCUMENTS

| | | | | |
|---|---|---|---|---|
| 4,406,290 A | * | 9/1983 | Walbeoffe-Wilson et al. | 600/502 |
| 5,359,513 A | * | 10/1994 | Kano et al. | 382/128 |
| 6,216,027 B1 | * | 4/2001 | Willis et al. | 600/424 |
| 6,708,052 B1 | * | 3/2004 | Mao et al. | 600/407 |
| 6,751,341 B2 | | 6/2004 | Oosawa | |
| 2001/0048757 A1 | | 12/2001 | Oosawa | |
| 2002/0006185 A1 | * | 1/2002 | Lienard et al. | 378/205 |

* cited by examiner

*Primary Examiner*—Eric F. Winakur
*Assistant Examiner*—Michael T. Rozanski
(74) *Attorney, Agent, or Firm*—Sughrue Mion, PLLC

(57) ABSTRACT

Obtainment of a present image, in which the arrangement of structural elements of a subject within the image approximates that of a past image of the same subject, and which is suitable for a temporal subtraction process, is enabled. A plurality of preliminary images of the subject are obtained, by a control unit controlling an imaging system constituted by an X-ray tube and an X-ray detector, to perform imaging at a plurality of imaging angles. An optimal imaging angle calculating unit calculates an optimal imaging angle, based on characteristic anatomical points of the subject that reflect changes in the subject's position, which is optimal for obtaining a present image having the least differences, due to the position of the subject, from a past image. The control unit controls the imaging system to perform imaging employing the optimal imaging angle.

17 Claims, 2 Drawing Sheets

RADIATION IMAGING APPARATUS

BACKGROUND OF THE INVENTION

1. Field of the Invention

The present invention relates to a radiation imaging apparatus. Specifically, the present invention relates to a radiation imaging device which is capable of obtaining past radiation images and present radiation images of a single subject, suitable for extracting differences between the two by inter image calculations, such as a so-called temporal subtraction process.

2. Description of the Related Art

There are known methods of detecting temporal changes in subjects, based on temporal subtraction images. The temporal subtraction images are obtained by performing inter image calculating processes, such as a subtraction process, on a radiation image of a subject which has been obtained in the past (hereinafter, referred to simply as "past image") and a radiation image of the same subject which is obtained presently (hereinafter, referred to simply as "present image"). The temporal subtraction image represents differences between the past image and the present image. In the field of medicine, for example, a method for detecting tumors that develop over time employing temporal subtraction images is known. This method obtains temporal subtraction images from past images and present images of the same subject, and detects the presence of new tumors based on the temporal subtraction images.

In cases in which temporal subtraction is performed, artifacts are generated unless the portions of the past images and present images that correspond to the subject are not completely matched (excluding the portions that have changed over time). The artifacts become barriers to the detection of temporal changes, therefore it is preferable that they are removed as much as possible.

Accordingly, methods for eliminating artifacts have been proposed, for example, in U.S. Patent Application Publication No. 20010048757 and U.S. Pat. No. 6,751,341. In these methods, image processes, such as affine transform, are administered on one or both of the past and present images, to match the positions of the images that correspond to the subject.

Factors that cause artifact generation include differences in the position of a subject. In the case that the subject is a living organism, the respiratory phase and the cardiac phase (the phase of the constriction/expansion movement of the heart) of the subject are also factors that contribute to artifact generation. For example, in the case that the subject is a human body, if the subject's position is different, positional misalignment as a whole, centered on the bone portions, is likely to occur. If the respiratory phase of the subject is different, the degree of inspiration differs, therefore the size of the lungs and the positions of the organs in the periphery thereof change, causing positional misalignment of the organs. Further, if the cardiac phase of the subject is different, the size of the heart and the arrangement of blood vessels in the periphery thereof differs, causing positional misalignment of the blood vessels.

In the positioning methods by the aforementioned image processes, rough positioning is possible, yet fine positioning of detailed elements is difficult, and there is a limit in the artifact eliminating capabilities thereof. Accordingly, it is difficult to detect fine elements, such as tumors having diameters of about 5 mm, which are indicative of the early stages of lung cancer.

A method can be considered, in which imaging conditions of a present image are aggressively controlled such that the arrangement of structural elements of the subject approximate that of a past image, thereby enabling the generation of temporal subtraction images having few artifacts. However, such a method has not yet been proposed.

SUMMARY OF THE INVENTION

The present invention has been developed in view of the above circumstances. It is an object of the present invention to provide a radiation imaging apparatus which is capable of obtaining present radiation images suitable for temporal subtraction processes, in which the arrangement of structural elements of the subject approximate that of a past image of the same subject.

The radiation imaging apparatus of the present invention comprises:

reference image input means, for inputting a reference radiation image of a subject in a predetermined respiratory phase;

preliminary imaging means, for imaging the subject, in a respiratory phase identical to the predetermined respiratory phase and in a predetermined imaging position, from a plurality of different imaging angles to obtain a plurality of preliminary images;

optimal imaging angle data calculating means, for calculating optimal imaging angle data, which represents an imaging angle that is optimal for obtaining radiation images having the least differences, due to the position of the subject, from the reference radiation image, based on difference data that represents a distance between characteristic anatomical points of the subject that reflects changes in the subject's position; and final imaging means, for radiographically imaging the subject with the optical imaging angle represented by the optimal imaging angle data to obtain a final radiation image of the subject.

Here the "subject" is a living organism which has a cardiopulmonary system.

The "predetermined respiratory phase" may be, for example, a maximum inspiration state, but is not limited thereto.

The "predetermined imaging position" is a position at which the relative positions of a radiation source, a radiation detector, and the subject assume a predetermined positional relationship (however, the orientations of the radiation source, the radiation detector, and the subject are not fixed).

The "respiratory phase identical to the predetermined respiratory phase" is not limited to a completely identical respiratory phase. States in which the respiratory phase differs from the predetermined respiratory phase within an allowable range of error during calculation of the optimal imaging angle data are also included.

The "imaging angle" refers to the angle of the optical axis, of radiation emitted from the radiation source to the subject, with respect to the subject, in a state in which the relative positions of the radiation source and the radiation detector are fixed (wherein the inclination of the radiation detector is also fixed).

The "preliminary imaging means" may be constituted, for example, by a combination of a radiation source and a radiation detector. In this case, the relative positions of the radiation source and the radiation detector with respect to each other are fixed, and the subject provided between the two. Preliminary images are obtained by performing radiographic imaging while moving the combination of the radiation source and the radiation detector relatively with respect to the subject, such that the imaging angle is varied in a stepwise manner in the vertical and the horizontal directions at a predetermined angular pitch. Alternatively, the "preliminary imaging means" may be constituted by a combination of a radiation source and a radiation detector, and an imaging table, on which the subject is placed. In this case, the combination of the radiation source and the radiation detector are fixed in position, and preliminary images are obtained by performing radiographic imaging while moving the imaging table, on which the subject is placed, relatively with respect to the combination, such that the imaging angle is varied in a stepwise manner in the vertical and the horizontal directions at a predetermined angular pitch.

Note that the preliminary imaging means may perform radiographic imaging with a lower radiation dosage than that employed during radiographic imaging by the final imaging means. For example, the radiation dosage employed by the preliminary imaging means may be about 1/10 to 1/100 of the radiation dosage employed by the final imaging means. The radiation dose received by the subject can be reduced by decreasing the radiation dosage employed during imaging in this manner.

The preliminary imaging means may also obtain the preliminary images at a coarser pixel size (widths in actual space that correspond to the width of each pixel) than that of the final radiation image. For example, if a pixel size of the final radiation image is set to be about 100 μm to 200 μm, the pixel size of the preliminary images may be set to be bout 400 μm to 1000 μm. By employing the coarser pixel size in this manner, the amount of time required to generate the preliminary images can be reduced, thereby enabling completion of imaging by the preliminary imaging means in a short time. Accordingly, the amount of time that the subject is required to maintain the predetermined respiratory phase is shortened, and the burden on the subject can be reduced.

The "distance between characteristic anatomical points of the subject that reflects changes in the subject's position" may be the distance between the leftmost end of the subject's left collarbone and the rightmost end of the subject's right collar bone, that reflects twisting of the subject in the horizontal direction. Alternatively, the "distance between characteristic anatomical points of the subject that reflects changes in the subject's position" may be the distance between characteristic anatomical points of the subject that reflects changes in the subject's position is the distance between the frontmost end of a predetermined rib of the subject and the rearmost end of the predetermined rib, that reflects inclination of the subject in the vertical direction. The frontmost end and the rearmost end of the predetermined rib may be distinguished by the direction of curvature thereof.

Note that here, "distance" refers to a distance relative to the size of the subject.

The characteristic anatomical points may be characteristic points which are present within different types of anatomical structural elements.

The characteristic anatomical points may be detected in each image by an image recognition process based on anatomical characteristics. Alternatively, the characteristic anatomical points may be detected based on difference data, obtained by inter image calculations administered on the reference image and the preliminary images. As examples of the "difference data", there are: ringing of bones or the ribcage; RMS within specified regions; and the like, within difference images obtained by inter image calculations administered on the reference image and the preliminary images.

Note that in the case that the pixel size of the preliminary images is coarse, the pixel size of the reference image may be converted to the same pixel size prior to administering the inter image calculations.

The "final imaging means" may be constituted, for example, by a combination of a radiation source and a radiation detector, similar to the preliminary imaging means. In this case, the relative positions of the radiation source and the radiation detector with respect to each other are fixed, and the subject provided between the two. Final radiation images are obtained by performing radiographic imaging while moving the combination of the radiation source and the radiation detector relatively with respect to the subject, such that the imaging angle is varied in a stepwise manner in the vertical and the horizontal directions at a predetermined angular pitch. Alternatively, the "final imaging means" may be constituted by a combination of a radiation source and a radiation detector, and an imaging table, on which the subject is placed. In this case, the combination of the radiation source and the radiation detector are fixed in position, and final radiation images are obtained by performing radiographic imaging while moving the imaging table, on which the subject is placed, relatively with respect to the combination, such that the imaging angle is varied in a stepwise manner in the vertical and the horizontal directions at a predetermined angular pitch.

Note that imaging systems (for example, a radiation source, a radiation detector, an imaging table, and the like) may be separately provided for the preliminary imaging means and the final imaging means, or the same imaging system may be commonly employed by the preliminary imaging means and the final imaging means.

The radiation imaging apparatus of the present invention may be of a configuration wherein:

respiratory phase data that represents the respiratory phase of the subject within the reference radiation image is attached to the reference radiation image; and the radiation imaging apparatus further comprises:

respiratory phase detecting means for detecting the respiratory phase of the subject;

matched respiratory phase detecting means, for detecting that the respiratory phase detected by the respiratory phase detecting means matches that represented by the respiratory phase data, and for outputting a detection signal; and detection data output means, for outputting data representing the detection, in response to the detection signal.

The "respiratory phase detecting means" may detect the respiratory phase of the subject by causing the subject to breathe through a bellows, and by measuring the length of the bellows, which changes according to the respiratory phase of the subject. Alternatively, the "respiratory phase detecting means" may detect the respiratory phase of the subject based on movements of the surface of the subject, captured by a CCD camera.

Here, the "matched respiratory phase detecting means" may output the detection signal continuously for the duration of the time that the respiratory phase of the subject matches that represented by the respiratory phase data. Alternatively, the detection signal may be output once, when the respiratory phase of the subject matches that represented by the respiratory phase data.

As examples of the "detection data output means", that which lights a lamp, that which outputs a noise or a voice message, and that which displays a message on a monitor may be considered.

The radiation imaging apparatus of the present invention may adopt a configuration wherein:

respiratory phase data that represents the respiratory phase of the subject within the reference radiation image is attached to the reference radiation image;

the radiation imaging apparatus further comprises:

respiratory phase detecting means for detecting the respiratory phase of the subject; and matched respiratory phase detecting means, for detecting that the respiratory phase detected by the respiratory phase detecting means matches that represented by the respiratory phase data, and for outputting a detection signal; and wherein:

the final imaging means performs radiographic imaging of the subject during a period in which the detection signal is being output.

Here, the "matched respiratory phase detecting means" outputs the detection signal continuously for the duration of the time that the respiratory phase of the subject matches that represented by the respiratory phase data.

The radiation imaging apparatus of the present invention having the above configuration may further adopt a configuration wherein:

cardiac phase data that represents the cardiac phase of the subject within the reference radiation image is attached to the reference radiation image;

the radiation imaging apparatus further comprises:

cardiac phase detecting means, for detecting the cardiac phase of the subject; and matched cardiac phase predicted period calculating means, for obtaining, based on the temporal changes of the cardiac phase detected by the cardiac phase detecting means, matched cardiac phase predicted period data that represents a period in which it is predicted that the cardiac phase of the subject will match that represented by the cardiac phase data; and wherein:

the final imaging means performs radiographic imaging during a period in which the detection signal is being output and during the matched cardiac phase predicted period, based on the matched cardiac phase predicted period data and the detection signal.

The "cardiac phase detecting means" may detect the cardiac phase of the subject by employing an EKG. Alternatively, the "cardiac phase detecting means" may be a heart rate monitor that detects the cardiac phase of the subject by detecting a pulse from a finger or a wrist of the subject with a sensor.

The referent of the phrase "respiratory phase detected by the respiratory phase detecting means matches that represented by the respiratory phase data" is not limited to cases in which the respiratory phases are strictly identical. The respiratory phase of the subject may be considered to be the same as that represented by the respiratory phase data as long as the degree of matching is within a range, which is determined according to the intended use of the final image. For example, assume a case in which a subtraction image, obtained by administering inter image calculations on the reference image and the final image, is observed to detect a predetermined significant point. The respiratory phase detected by the respiratory phase detecting means (the respiratory phase of the subject within the final image) and the respiratory phase represented by the respiratory phase data (the respiratory phase of the subject within the reference image) are recognized as being the same as long as the degree of matching is within a range that does not cause artifacts, due to the difference in respiratory phase, that interfere with detection of the significant point.

The referent of the phrase "cardiac phase of the subject will match that represented by the cardiac phase data" is not limited to cases in which the cardiac phases are strictly identical. In a manner similar to that of the respiratory phase, the cardiac phase of the subject may be considered to be the same as that represented by the cardiac phase data as long as the degree of matching is within a range, which is determined according to the intended use of the final image.

The radiation imaging apparatus of the present invention images the subject from a plurality of different imaging angles to obtain a plurality of preliminary images. Next, an optimal imaging angle is calculated, based on difference data that represents a distance between characteristic anatomical points of the subject that reflects changes in the subject's position, which is optimal for obtaining radiation images having the least differences, due to the position of the subject, from the reference radiation image. Then, final imaging is performed employing the optimal imaging angle. Therefore, misalignment of the subject's position between a past imaging operation and a present imaging operation can be absorbed by adjustment of the imaging angle. Accordingly, a present radiation image, in which the arrangement of structural elements of the subject approximates that of the reference image obtained in the past and is suitable for a temporal subtraction process, can be obtained.

DESCRIPTION OF THE PREFERRED EMBODIMENTS

Hereinafter, an embodiment of the radiation imaging apparatus according to the present invention will be described.

Figure 1:
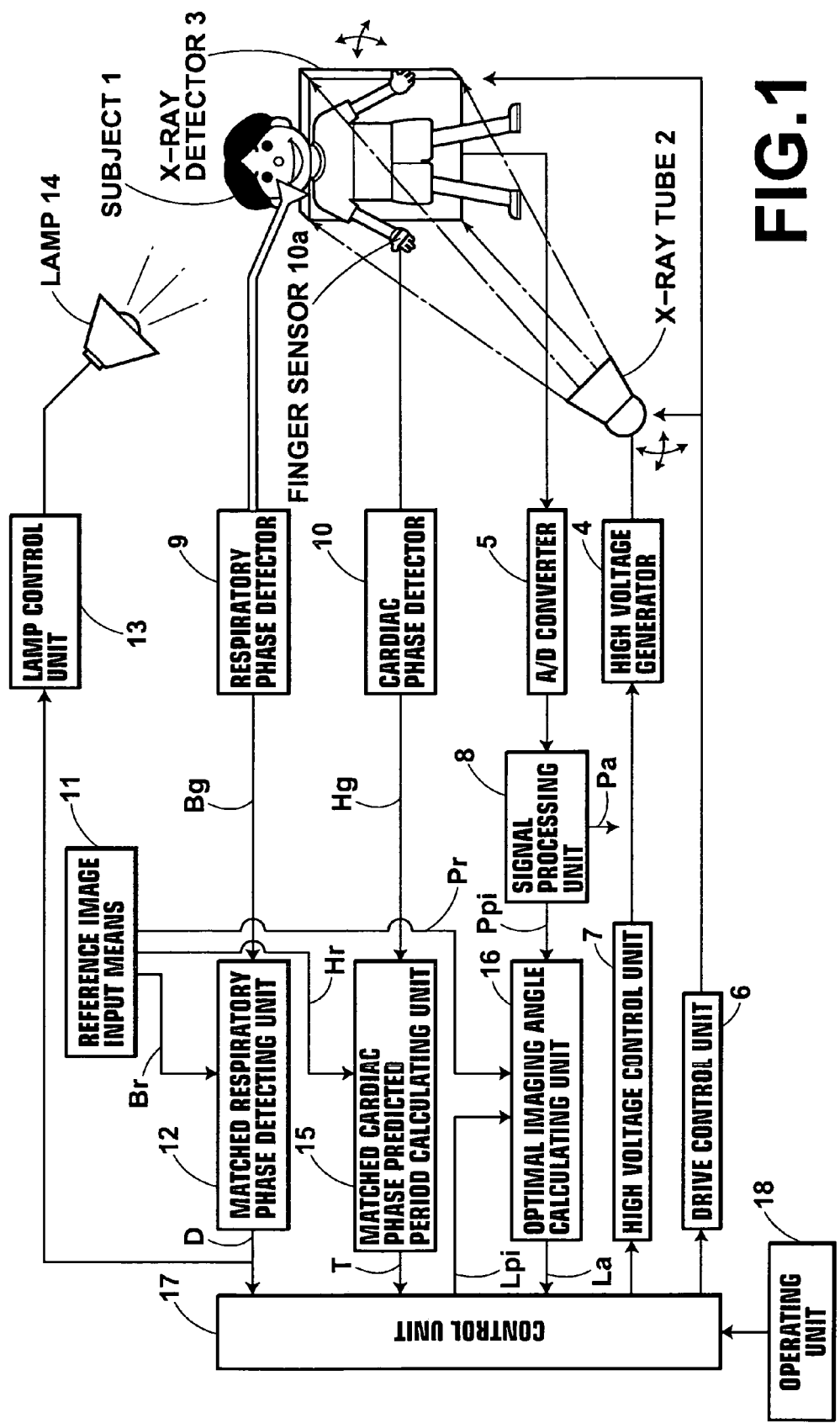
FIG. 1 is a block diagram illustrating the construction of an X-ray imaging apparatus, which is an embodiment of the radiation imaging apparatus of the present invention.

FIG. 1 is a block diagram illustrating the construction of an X-ray imaging apparatus, which is an embodiment of the radiation imaging apparatus of the present invention. The x-ray imaging apparatus illustrated in FIG. 1 comprises: an X-ray tube 2, for irradiating X-rays onto a human subject 1; an X-ray detector 3, such as a flat panel detector, for photoelectrically detecting X-rays and for outputting analog electrical signals; a high voltage generator 4, for applying high voltage to the X-ray tube 2; an A/D converter 5, for converting the analog electrical signals output from the X-ray detector 3 into digital signals and for outputting the digital signals; a drive control unit 6, for driving a drive unit (not shown) to control the positions and inclinations of the X-ray tube 2 and the X-ray detector 3; a high voltage control unit 7, for controlling the voltage generated by the high voltage generator 4 and applied to the X-ray tube 2; a signal processing unit 8, for converting the digital signals output from the A/D converter to image data and generating preliminary image data sets Ppi (i=1, 2, . . . ) that represent a plurality of preliminary images Ppi and a final image data set Pa that represents a final image Pa; a respiratory phase detector 9, for detecting the present respiratory phase Bg of the subject 1 and for outputting a present respiratory phase signal Bg; a cardiac phase detector 10, for detecting the present cardiac phase Hg of the subject 1 and for outputting a present cardiac phase signal Hg; a reference image input means 11, for inputting a reference image data set Pr that represents a reference image Pr, which is a radiation image of the subject 1 obtained in the past, and to which reference respiratory phase data Br that represents the reference respiratory phase Br of the subject within the reference image Pr and reference cardiac phase data Hr that represents the reference cardiac phase Hr of the subject 1 within the reference image Pr are attached; a matched respiratory phase detecting unit 12, for detecting that the reference respiratory phase Br and the present respiratory phase Bg are matched, based on the reference respiratory phase data Br attached to the reference image Pr input by the reference image input means 11 and the present respiratory phase signal Bg output from the respiratory phase detector 9, and for continuously outputting a matched respiratory phase signal D for the duration of the time that the respiratory phases are matched; a lamp control unit 13, for lighting a lamp 14 while the matched respiratory phase signal D is being output by the matched respiratory phase detecting unit 12; a matched cardiac phase predicted period calculating unit 15, for calculating a time period in which the reference cardiac phase Hr and the present cardiac phase Hg will match, based on the reference cardiac phase data Hr attached to the reference image Pr input by the reference image input means 11 and the temporal changes of the present cardiac phase signal Hg output from the cardiac phase detector 10, and for outputting a matched cardiac phase signal T synchronous with a time period, during which the cardiac phase of the subject 1 is predicted to match the reference cardiac phase Hr; an optimal imaging angle calculating unit 16, for calculating optimal imaging angle data La that represents an optimal imaging angle La which is optimal for obtaining radiation images having the least differences, due to the position of the subject, from the reference radiation image, by employing the reference image data set Pr and the plurality of preliminary image data set Ppi to derive differences in the distances between characteristic anatomical points that represent changes in the subject's position, among the reference image Pr and each of the preliminary images Ppi, and calculating the optimal angle data La, based on the imaging angles Lpi of each of the preliminary images Ppi and the differences; a control unit 17, for performing overall control, such as controlling the drive control unit 6 to arrange the X-ray tube 2 and the X-ray detector 3 in predetermined imaging positions in order to perform preliminary imaging with the plurality of imaging angles Lpi and to perform final imaging with the optimal imaging angle La, and controlling the high voltage control unit 7 to set the radiation dosage of X-rays and irradiation timings thereof; and an operating unit 18, for inputting various types of data via a keyboard, a mouse, and the like.

Note that the X-ray tube 2, the X-ray detector 3, the High voltage generator 4, the A/D converter 5, the drive unit (not shown), the drive control unit 6, the high voltage control unit 7, the signal processing unit 8 and the control unit 17 constitute preliminary imaging means and final imaging means of the present invention.

Note also that the same reference numerals and letters will be employed to represent phases, images, and signals as well as the data that represents the phases, images, and signals.

Next, the operation of the X-ray imaging apparatus illustrated in FIG. 1 will be described, using a case in which a human thorax is X-rayed to obtain a chest x-ray image which is suitable for a temporal subtraction process as an example.

First, a reference image data set Pr that represents a reference image Pr of a subject 1, in which the subject is in a respiratory phase close to maximum inspiration, is input by the reference image input means 11. The reference image data set Pr is read out from a database or a recording medium (not shown). The reference respiratory phase data Br that represents the respiratory phase of the subject within the reference image Pr and the reference cardiac phase data Hr that represents the reference cardiac phase of the subject within the reference image Pr are attached to the reference image data set Pr.

Meanwhile, the X-ray tube 2 and the X-ray detector 3 are arranged in an imaging position for performing normal chest X-ray imaging. That is, the X-ray tube 2 and the X-ray detector 3 are spaced at an interval appropriate for chest X-ray imaging, and the subject 1 is placed such that the subject's thorax is close to a detecting surface of the X-ray detector 3.

When the arrangement of the imaging position is complete, the subject 1 is caused to adjust their respiratory phase to approximate a maximum inspiration phase, in order to prepare for preliminary imaging.

When preparations for preliminary imaging are complete, a command to initiate preliminary imaging is input by the operating unit 18. Then, the control unit 17 controls the drive control unit 6 to control the drive unit (not shown) to move the imaging system, consisting of the X-ray tube 2 and the X-ray detector 3, relatively with respect to the subject 1 placed therebetween, while maintaining the positional relationship between the X-ray tube 2 and the X-ray detector 3 (the inclination of the detecting surface of the X-ray detector 3 is also maintained with respect to the X-ray tube 2). Thereby, the imaging angle with respect to the subject 1 is varied in a stepwise manner in the vertical and the horizontal directions at a predetermined angular pitch. At the same time, the control unit 17 controls the high voltage control unit 7 to control voltages applied to the X-ray tube 2 as well as voltage application timings. Thereby, the subject 1 is irradiated with X-rays at each imaging angle Lpi, and the X-rays that have passed through the subject 1 are detected by the X-ray detector 3, that is, preliminary imaging is performed. The imaging angle is changed in five steps in the vertical direction and five steps in the horizontal direction at an angular pitch of five degrees, for example. The X-ray dosage is set at $\frac{1}{10}$ to $\frac{1}{100}$ of that which will be employed in the final imaging, which will be performed later. The image quality of X-ray images generally improves with an increase in the X-ray dosage. However, the preliminary images that are obtained by the preliminary imaging need only to be of an image quality that enables discrimination of anatomical structural elements of the subject 1. Therefore, the X-ray dosage is reduced, to decrease the X-ray dosage that the subject 1 is exposed to.

The X-ray detector 3 photoelectrically detects the X-rays which have passed through the thorax of the subject 1, and outputs analog electrical signals corresponding to each irradiation of the X-rays.

The A/D converter 5 converts each of the analog electrical signals output by the X-ray detector into digital signals. The signal processing unit 8 generates image data sets based on the digital signals for each irradiation of the X-rays, that is, for each imaging operation. Thereby, preliminary image data sets Ppi that represent the plurality of preliminary images Ppi, which have different imaging angles, are obtained. The preliminary images which are obtained at this time have larger pixel sizes than that of the final image, in order to cause the preliminary images to be coarser than the final image. For example, if the pixel size of the final radiation image is set to be about 100 μm to 200 μm, the pixel size of the preliminary images may be set to be bout 400 μm to 1000 μm. By employing the coarser pixel size in this manner, the amount of time required to generate the preliminary images (readout of the signals) can be reduced, thereby enabling completion of imaging by the preliminary imaging means in a short time. Accordingly, the amount of time that the subject is required to maintain the predetermined respiratory phase is shortened, and the burden on the subject can be reduced. The preliminary image data sets Ppi, which have been obtained in this manner, are sent to the optimal imaging angle calculating unit 16.

The optimal imaging angle calculating unit 16 extracts difference data that represents differences, in the distances between characteristic anatomical points of the subject 1 that reflect changes in the subject's position, between the reference image Pr and the plurality of preliminary images Pp1, Pp2, Pp3 . . . . The optimal imaging angle calculating unit 16 extracts the difference data based on the reference image data set Pr and the plurality of preliminary image data sets Ppi. The optimal imaging angle calculating unit calculates an optimal angle La, at which an image having the least differences, due to the position of the subject, can be obtained, based on the difference data. Specifically, first, inter image calculations are performed between the reference image Pr and each of the preliminary images Ppi that have different imaging angles in the horizontal direction. Difference images that represent the differences among the images are generated, and artifacts of the collarbones that reflect twisting of the subject 1 in the horizontal direction are discriminated. The differences in the distances between the leftmost end of the left collarbone and the rightmost end of the right collarbone are derived from the sizes and directions of the artifacts. The optimal imaging angle in the horizontal direction is calculated, based on the differences within each of the difference images corresponding to each of the preliminary images and the imaging angle of each of the preliminary images. Meanwhile, inter image calculations are performed between the reference image Pr and each of the preliminary images Ppi that have different imaging angles in the vertical direction. Difference images that represent the differences among the images are generated, and artifacts of the ribs that reflect twisting of the subject 1 in the vertical direction are discriminated. The differences in the distances between the frontmost end and a rearmost end of a predetermined rib are derived from the sizes and directions of the artifacts. The optimal imaging angle in the vertical direction is calculated, based on the differences within each of the difference images corresponding to each of the preliminary images and the imaging angle of each of the preliminary images. The optimal imaging angle data La that represents an optimal imaging angle La is calculated, based on the optimal imaging angles in the horizontal and vertical directions.

Figure 2A:
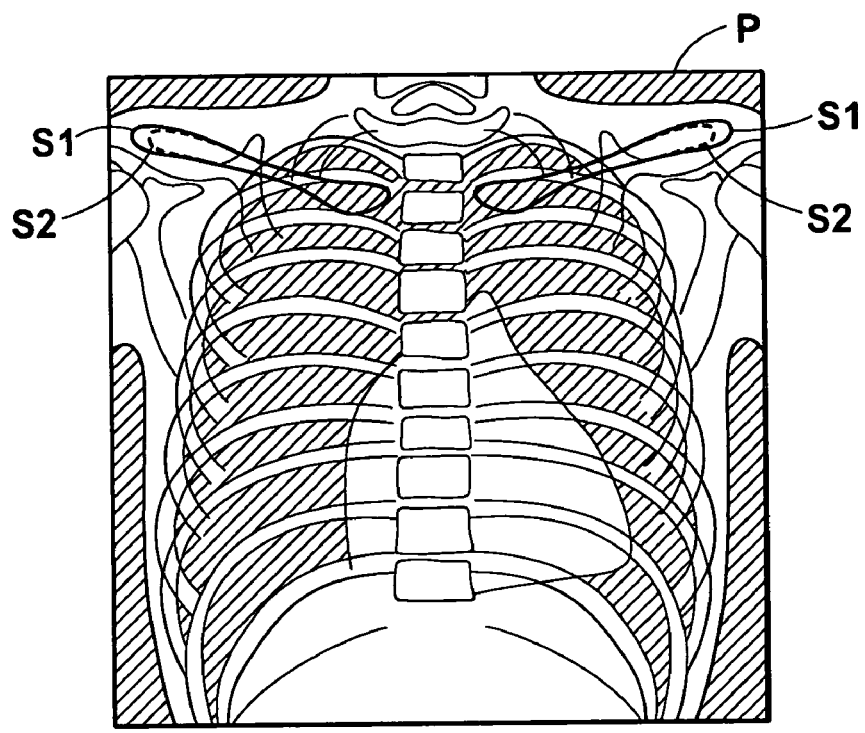
FIGS. 2A and 2B illustrate changes of characteristic anatomical points of a subject within a chest X-ray image, due to differences in the subject's position.
Figure 2B:
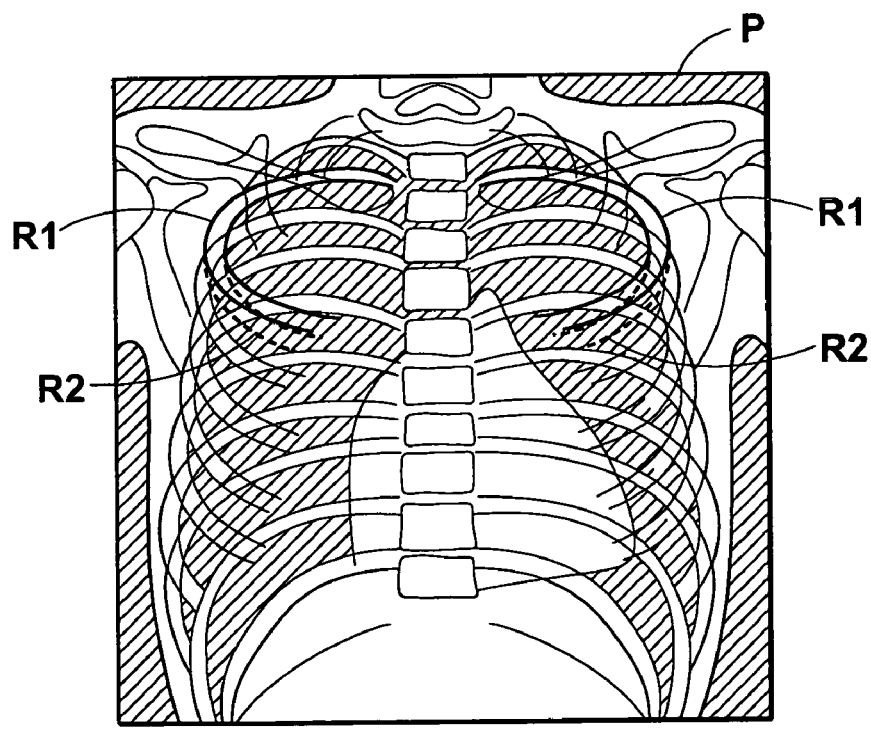

FIG. 2A is a diagram that illustrates a change in the arrangement of the subject's collarbones within a chest X-ray image P, due to twisting of the subject in the horizontal direction. In FIG. 2A, S1 and S2 denote collarbones in states of different degrees of twisting. The collarbones appear longest in the X-ray image in a state in which the subject is not twisted at all. As the degree of twisting increases, the collarbones appear shorter within the X-ray image. Even if the subject is twisted in this manner, an image, in which the subject is twisted at a degree of twisting similar to that within the reference image is able to be obtained, by adjusting the imaging angle in the horizontal direction. FIG. 2B is a diagram that illustrates a change in the arrangement of the subject's ribs within the chest X-ray image P, due to the subject's inclination in the vertical direction. In FIG. 2B, R1 and R2 denote ribs in states of different degrees of inclination. The distance between the frontmost end and the rearmost end of a rib appear shorter or longer, depending on the degree of inclination of the subject in the vertical direction. Even if the subject is inclined in this manner, an image, in which the subject is inclined at a degree of inclination similar to that within the reference image is able to be obtained, by adjusting the imaging angle in the vertical direction.

Note that when inter image calculations are administered on the reference image Pr and the preliminary images Ppi, the reference image Pr is processed so that the pixel size thereof is matched to those of the preliminary images.

After the optimal imaging angle data La is calculated, the control unit 17 controls the drive control unit 6 to control the drive unit (not shown). The drive unit (not shown) moves the combined imaging system, consisting of the X-ray tube 2 and the X-ray detector 3, so that the imaging system is positioned to perform imaging at the optimal imaging angle La, represented by the optimal imaging angle data La. Thereby, differences, due to changes in the position of the subject 1 between that in the reference image Pr and a present imaging operation, can be absorbed by adjusting the imaging angle.

The respiratory phase detector 9 detects the respiratory phase of the subject 1, by detecting the length of a bellows, which is attached to the subject's mouth and the length of which changes according to the respiratory phase of the subject 1. The respiratory phase detector 9 continuously outputs a present respiratory phase signal Bg that represents the present respiratory phase of the subject 1.

The matched respiratory phase detecting unit 12 detects that the present respiratory phase Bg of the subject 1 matches the reference respiratory phase Br, based on the reference respiratory phase data Br attached to the reference image data Pr and the present respiratory phase signal Bg. When it is detected that the present respiratory phase Bg and the reference respiratory phase Br are matched, the matched respiratory phase detecting unit 12 outputs the matched respiratory phase signal D.

The lamp control unit 13 lights the lamp 14 while the matched respiratory phase signal D is being output. An operator of the X-ray imaging apparatus and the subject 1 are informed that the present respiratory phase Bg matches the reference respiratory phase Br by the lighting of the lamp 14. Therefore, the operator is enabled to urge the subject 1 to adjust their breathing, or the subject 1 is enabled to adjust their own breathing accordingly.

The control unit 17 monitors the matched respiratory phase signal D, and controls the X-ray imaging apparatus such that final imaging is enabled only while the matched respiratory signal D is being output. That is, control is performed such that imaging is allowed only during a period in which the respiratory phase of the subject 1 is matched with the respiratory phase of the subject 1 in the reference image Pr, and not allowed at other times. Thereby, misalignment of the structural elements within the subject 1, due to differences in the respiratory phase of the subject 1, is suppressed.

The cardiac phase detector 10 detects the cardiac phase of the subject 1, by detecting the subject's pulse with a sensor, which is attached to a finger of the subject 1. The cardiac phase detector 10 continuously outputs a present cardiac phase signal Hg that represents the present cardiac phase of the subject 1.

The matched cardiac phase detecting unit 15 predicts a time period in which the present cardiac phase Hg of the subject 1 matches the reference respiratory phase Hr, based on the reference cardiac phase data Hr attached to the reference image data Pr and temporal changes in the subject's cardiac phase, obtained from the present cardiac phase signal Hg. The matched cardiac phase signal T is output synchronous with a time period, during which the cardiac phase of the subject 1 is predicted to match the reference cardiac phase Hr.

The control unit 17 monitors the matched cardiac phase signal T, and controls the X-ray imaging apparatus such that final imaging is enabled only while the matched cardiac signal T is being output. That is, control is performed such that imaging is allowed only during a period in which the cardiac phase of the subject 1 is matched with the cardiac phase of the subject 1 in the reference image Pr. Thereby, misalignment of the structural elements within the subject 1, due to differences in the cardiac phase of the subject 1, is suppressed.

Accordingly, the control unit 17 controls the high voltage control unit 7 to irradiate the subject with X-rays at the final imaging radiation dosage when both the respiratory phase and the cardiac phase of the subject 1 are matched to those within the reference image Pr, to perform final imaging.

Thereafter, the X-ray detector 3 photoelectrically detects the X-rays that have passed through the subject 1, and final image data Pa that represents the final image Pa is generated via the A/D converter and the signal processing unit 8.

In this manner, the X-ray imaging apparatus of the present invention preliminarily images the subject 1 from a plurality of different imaging angles by the control unit 17 controlling the imaging system, consisting of the X-ray tube 2 and the X-ray detector 3, to obtain a plurality of preliminary images Ppi. Next, an optimal imaging angle La is calculated, based on characteristic anatomical points of the subject that reflect changes in the subject's position, which is optimal for obtaining a present image Pa having the least differences, due to the position of the subject 1, from the reference radiation image Pr, which is a past image. Then, the control unit 17 controls the imaging system to perform final imaging employing the optimal imaging angle La. Therefore, misalignment of the subject's position between a past imaging operation and a present imaging operation can be absorbed by adjustment of the imaging angle. Accordingly, a present radiation image Pa, in which the arrangement of structural elements of the subject 1 approximates that of the reference image Pr obtained in the past and is suitable for a temporal subtraction process, can be obtained.

Further, the X-ray imaging apparatus detects the present respiratory state Bg and the present cardiac state Hg of the subject 1. The X-ray imaging apparatus controls imaging operations so that the respiratory phase and the cardiac phase of the subject 1 approximate those within the reference image Pr, by utilizing the detected respiratory phase Bg, the detected cardiac phase Hg, the reference respiratory phase data Br, and the reference cardiac phase data Hr. Accordingly, a present radiation image Pa, in which the arrangement of structural elements of the subject 1 further approximates that of the reference image Pr obtained in the past and is more suitable for a temporal subtraction process, can be obtained.

Note that in the present embodiment, final imaging is performed when the subject's present respiratory phase Bg and the present cardiac phase Hg matches the respiratory phase and the cardiac phase within the reference image Pr. It goes without saying that final imaging may be performed depending on how close the state of the subject 1 approximates that within the reference image Pr, according to both the respiratory and cardiac phases. Alternatively, control of final imaging according to the cardiac phase may be omitted, and final imaging may be performed only according to the respiratory phase.

In addition, in the present embodiment, the imaging angle was varied in a stepwise manner in the horizontal and vertical directions during preliminary imaging. Alternatively, the imaging angle may be varied in a stepwise manner in an oblique direction, or varied in a stepwise manner along a lattice incorporating the vertical and horizontal directions at a predetermined angular pitch.

What is claimed is:

1. A radiation imaging apparatus, comprising:
    reference image input means for inputting a reference radiation image of a subject in a predetermined respiratory phase;
    preliminary imaging means for imaging the subject, who is in the same predetermined respiratory phase and in a predetermined imaging position, from a plurality of different imaging angles to obtain a plurality of preliminary images;
    optimal imaging angle data calculating means for calculating optimal imaging angle data, which represents an imaging angle that is optimal for obtaining radiation images having the least differences, due to the position of the subject, from the reference radiation image, based on difference data obtained from said plurality of preliminary images that represents a distance between characteristic anatomical points of the subject that reflects changes in the subject's position; and
    final imaging means for radiographically imaging the subject with the optical imaging angle represented by the optimal imaging angle data to obtain a final radiation image of the subject.

2. A radiation imaging apparatus as defined in claim 1, wherein:
    respiratory phase data that represents the respiratory phase of the subject within the reference radiation image is attached to the reference radiation image; and
    the radiation imaging apparatus further comprises:
    respiratory phase detecting means for detecting the respiratory phase of the subject;
    matched respiratory phase detecting means for detecting that the respiratory phase detected by the respiratory phase detecting means matches that represented by the respiratory phase data, and for outputting a detection signal; and
    detection data output means for outputting data representing the detection, in response to the detection signal.

3. A radiation imaging apparatus as defined in claim 2, wherein:
    the respiratory phase detecting means detects the respiratory phase of the subject by causing the subject to breathe through a bellows, and by measuring the length of the bellows, which changes according to the respiratory phase of the subject.

4. A radiation imaging apparatus as defined in claim 2, wherein:
    the respiratory phase detecting means detects the respiratory phase of the subject, based on movements of the surface of the subject, captured by a CCD camera.

5. A radiation imaging apparatus as defined in claim 2, wherein:
    the detection data output means outputs the detection data by employing one of lighting a lamp; outputting an audio message, and displaying a message on a monitor.

6. A radiation imaging apparatus as defined in claim 2, wherein:
    the respiratory phase data represents the subject at maximum inhalation.

7. A radiation imaging apparatus as defined in claim 1, wherein:
    respiratory phase data that represents the respiratory phase of the subject within the reference radiation image is attached to the reference radiation image;
    the radiation imaging apparatus further comprises:
    respiratory phase detecting means for detecting the respiratory phase of the subject; and
    matched respiratory phase detecting means for detecting that the respiratory phase detected by the respiratory phase detecting means matches that represented by the respiratory phase data, and for outputting a detection signal; and wherein:

the final imaging means performs radiographic imaging of the subject during a period in which the detection signal is being output.

8. A radiation imaging apparatus as defined in claim 7, wherein:

cardiac phase data that represents the cardiac phase of the subject within the reference radiation image is attached to the reference radiation image;

the radiation imaging apparatus further comprises:

cardiac phase detecting means for detecting the cardiac phase of the subject; and matched cardiac phase predicted period calculating means, for obtaining, based on the temporal changes of the cardiac phase detected by the cardiac phase detecting means, matched cardiac phase predicted period data that represents a period in which it is predicted that the cardiac phase of the subject will match that represented by the cardiac phase data; and wherein:

the final imaging means performs radiographic imaging during a period in which the detection signal is being output and during the matched cardiac phase predicted period, based on the matched cardiac phase predicted period data and the detection signal.

9. A radiation imaging apparatus as defined in claim 8, wherein:

the cardiac phase detecting means detects the cardiac phase of the subject by employing an EKG.

10. A radiation imaging apparatus as defined in claim 8, wherein:

the cardiac phase detecting means detects the cardiac phase of the subject by detecting a pulse from a finger or a wrist of the subject with a sensor.

11. A radiation imaging apparatus as defined in claim 7, wherein:

the respiratory phase detecting means detects the respiratory phase of the subject by causing the subject to breathe through a bellows, and by measuring the length of the bellows, which changes according to the respiratory phase of the subject.

12. A radiation imaging apparatus as defined in claim 7, wherein:

the respiratory phase detecting means detects the respiratory phase of the subject, based on movements of the surface of the subject, captured by a CCD camera.

13. A radiation imaging apparatus as defined in claim 1, wherein:

the subject is a human body; and the distance between characteristic anatomical points of the subject that reflects changes in the subject's position is the distance between the leftmost end of the subject's left collarbone and the rightmost end of the subject's right collar bone, that reflects twisting of the subject in the horizontal direction.

14. A radiation imaging apparatus as defined in claim 1, wherein:

the subject is a human body; and the distance between characteristic anatomical points of the subject that reflects changes in the subject's position is the distance between the frontmost end of a predetermined rib of the subject and the rearmost end of the predetermined rib, that reflects inclination of the subject in the vertical direction.

15. A radiation imaging apparatus as defined in claim 1, wherein:

the preliminary imaging means performs radiographic imaging with a lower radiation dosage than that employed during radiographic imaging by the final imaging means.

16. A radiation imaging apparatus as defined in claim 1, wherein:

the plurality of different imaging angles is varied in stepwise manner in a vertical and horizontal direction.

17. A radiation imaging apparatus as defined in claim 1, wherein:

the imaging angle that is optimal refers to an angle of an optical axis of radiation emitted to the subject, in a state in which a relative position of a radiation source and a radiation detector are fixed.

\* \* \* \* \*